United States Patent [19]

Brown

[11] Patent Number: 4,866,181

[45] Date of Patent: Sep. 12, 1989

[54] PROCESS FOR PRODUCING OPTICALLY ACTIVE ALCOHOLS

[75] Inventor: Herbert C. Brown, West Lafayette, Ind.

[73] Assignee: Aldrich-Boranes, Inc., Milwaukee, Wis.

[21] Appl. No.: 134,463

[22] Filed: Dec. 17, 1987

Related U.S. Application Data

[62] Division of Ser. No. 902,175, Aug. 29, 1986, Pat. No. 4,772,752.

[51] Int. Cl.$^4$ .................... C07C 27/04; C07C 29/136; C07F 5/02

[52] U.S. Cl. ........................ 546/348; 568/6; 568/808; 568/814; 568/817; 568/820; 568/832; 568/838; 568/884; 549/29

[58] Field of Search ................... 568/6, 814, 832, 808, 568/817, 820, 838, 884; 546/348; 549/29

[56] References Cited

U.S. PATENT DOCUMENTS 4,078,002  3/1978  Brown ................................ 568/832

OTHER PUBLICATIONS

Brown et al, J. Am. Chem. Soc., 105, pp. 2092–2093 (1983).

Brown et al, Tetrahedron 37, pp. 3547–3587, 1981.

*Primary Examiner*—Donald B. Moyer
*Assistant Examiner*—Karen E. Kulesza
*Attorney, Agent, or Firm*—Niblack & Niblack

[57] ABSTRACT

A process for preparing optically active alcohols by reducing ketones using mono- or diisopinocampheyl-haloboranes as reducing agents.

9 Claims, No Drawings

PROCESS FOR PRODUCING OPTICALLY ACTIVE ALCOHOLS

This is a division of application Ser. No. 902,175, filed Aug. 29, 1986, now U.S. Pat. No. 4,772,752, issued Sept. 20, 1988.

BACKGROUND OF THE INVENTION

The reduction of prochiral ketones produces an alcohol which contains an asymmetric carbon atoms, designated by the asterik in the following reaction.

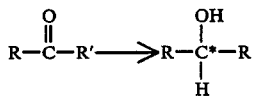

Considerable effort has been expended in the past and continues to be expended in finding asymmetric reducing agents which will achieve the reduction of such carbonyl groups to give optically active alcohols of high optical purity (100% optical purity=100% ee).

One valuable reagent is B-isopinocampheyl-9-borabicyclo[3.3.1]nonane, B-Ipc-9-BBN, made by hydroborating optically active α-pinene with 9-borabicyclo[3.3.1.]nonane (9-BBN) and sold by Aldrich Chemical Company under the registered trademark Alpine-Borane, and the modified borohydride reagent, NB-Enantride [M. M. Midland, A. Kazubski, *J. Org. Chem.*, 47, 2495 (1982).

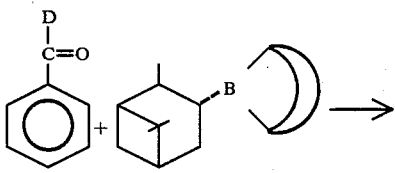

This reagent readily reacts with deuteroaldehydes, RCDO, to give the reduced product, a primary alcohol, in optical purities approaching 100% [M. M. Midland, S. Greer, A. Tramontano, S. A. Zderic, *J. A. Chem. Soc.*, 47, 2352 (1979)].

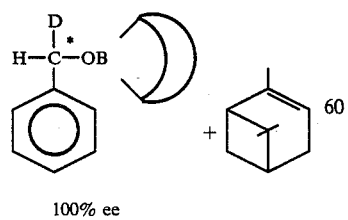

100% ee

The α-pinene can be recovered and reused.

Originally, this reagent gave very poor results in the reduction of ketones. [A. Tramontano, Ph.D. Thesis, U. Cal. Riverside, 1980)], resulting in end product of only 7% optical purity.

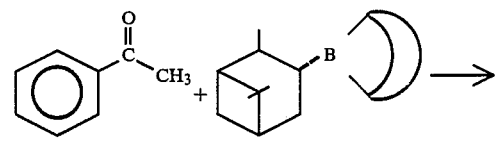

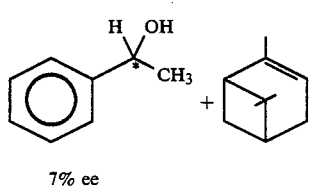

7% ee

However, it does reduce acetylenic ketones in high optical purity [M. M. Midland, A. Tramontano, A. Kazubski, R. S. Graham, D. S. Tsai, D. B. Cardin, Tetrahedron, 40, 1371 (1984)].

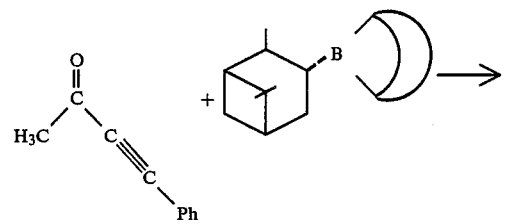

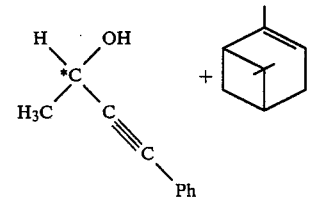

Another modified borohydride reagent, K 9-O-DIPGF-9-BBNH is highly promising. [H. C. Brown, W. S. Park and B. T. Cho, *J. Org. Chem.*, 51, 0000 (1986).

In addition, an enzymatic chiral reduction of ketones was recently reported by E. Keinan, E. K. Hafeli, K. K. Seth and R. Lamed, *J. Am. Chem. Soc.*, 108, 162 (1986).

It still remains highly desirable to find a reagent that will do equally well in reducing aliphatic, alicyclic, and aromatic ketones. Indeed, it was discovered that carrying out the reaction under neat conditions or concentrated solutions provided product having 87% optical purity. [H. C. Brown and G. G. Pai, *J. Org. Chem.*, 50, 1384 (1985).

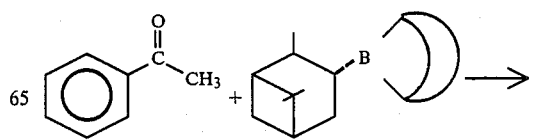

-continued

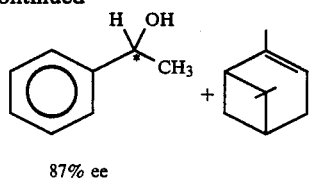

87% ee

Even better results (94% optical purity) can be realized by carrying out the reduction under exceptionally high pressures, 6000 atmos. [M. M. Midland and J. I. McLoughlin, J. Org. Chem., 49, 1317 (1984)].

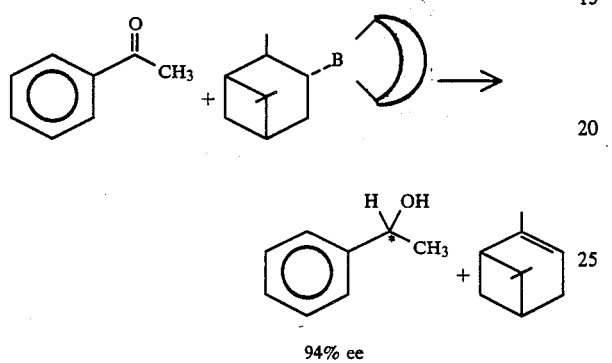

94% ee

Nevertheless, there remains a longstanding need for reagents which have an exceptional ability to achieve the reduction of many types of ketones in very high optical purities under very simple conditions. The present invention provides such reagents.

SUMMARY OF THE INVENTION

The present invention provides novel mono- and diisopinocampheylhaloboranes, represented by the formulae IpcBX$_2$ and Ipc$_2$BX wherein Ipc is isopinocampheyl and X is halo.

The term "halo", as used herein, refers to chloro, fluoro, bromo and iodo.

The compounds of this invention may also be represented by the formulae

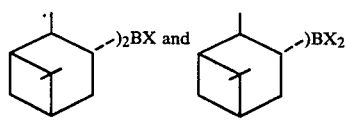

In addition, the present invention provides novel organoboron halides of the formula:

R*BX$_2$ and

R*$_2$BX wherein R* is is an optically active organo group with borane directly attached to the asymmetric center of said organo group and X is halo as defined above.

The optically active boron halides of the present invention are optically stable over reasonable periods of time. Moreover, some of them are exceptionally reactive reducing agents, reacting far faster with carbonyl compounds than 9-B-isopinocampheylbicyclo[3.3.1]nonane.

Generally speaking, the boron halides of this invention are prepared according to the following illustrative reaction schemes.

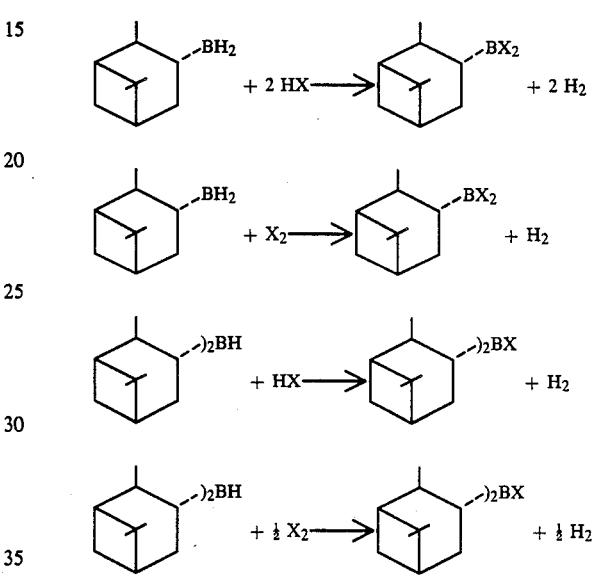

In general, the more active halogens, fluorine and chlorine, are best used as the hydrogen halide, HF and HCl. The least reactive halogen, iodine, is best used as the halogen. Bromine can be used in either form.

The presently preferred boron halide is diisopinocampheylchloroborane, a remarkably efficient chiral reducing agent for aromatic prochiral ketones (aralkyl and heteroaralkyl ketones) and α-tertiary alkyl ketones having superior optical purities than those obtained by prior art methods and reagents.

DETAILED DESCRIPTION OF PREFERRED EMBODIMENTS

The following examples further illustrate the present invention. All operations werer carried out under nitrogen. Unless otherwise indicated, optical rotations were measured at 20° C.

EXAMPLE 1

Preparation of Diisocampheylchloroborane

Diisopinocampheylborane, prepared from (+)-α-pinene (230 mmol) and BH$_3$.SMe$_2$ (100 mmol) in tetrahydrofuran (THF) (96 mL) at 0° C. by the method of H. C. Brown et al, *J. Org. Chem.*, 47, 5065 (1982), was suspended in ethyl ether (50 mL) at −78° C. Dry hydrogen chloride in ethyl ether (1 equiv., calculated for the amount of Ipc$_2$BH) was added. After being stirred for 15 minutes at −78° C., the reaction mixture was warmed to 0° C. and stirred at that temperature until all of the solid dissolved and gas evolution ceased (2 h). $^{11}$B NMR showed a single peak at 76 ppm (relative to BF$_3$.OEt$_2$). Upon removal of the ether solvent and cooling, diisopinocampheylchloroborane solidified (mp 54°-56° C. after crystallization from pentane.) The overall yield based on BH$_3$.SMe$_2$ is 75% [α]$_D$−67.07° (c 13.5, CH$_2$Cl$_2$).

EXAMPLE 2

Preparation of Diisopinocampheylbromoborane

Diisopinocampheylbromoborane was prepared in two ways. (1) By reacting Ipc$_2$BH with HBr in ether and (2) by reacting Ipc$_2$BH with Br$_2$ as follows.

(1) HBr in ether was prepared by passing the gas from a lecture bottle through ice cold ether. The solution was standardized by titration with an aliquot with standard NaOH. To Ipc$_2$BH (19.0 g, 66.5 mmol) cooled to −78° C. in a 250 mL round-bottom flask under a nitrogen atmosphere was added ether (50 mL), followed after 15 minutes by 21.38 mL of 3.11 N HBr in ether. After stirring for another 15 min. at −78° C., the mixture was brought to 0° C. and stirred until all of the Ipc$_2$BH dissolved. $^{11}$B NMR showed a broad singlet at δ80.00 (Ipc$_2$BBr). Following methanolysis, the product showed a broad singlet at δ53.00 (Ipc$_2$BOMe). The ether was pumped off to obtain a white solid in a yield of 21.47 g (88%).

(2) Diisopinocampheylborane was prepared in ether, crystallized out, the excess α-pinene and ether removed and the crystals washed with ice cold ether and dried under vacuum. (Preparation of Ipc$_2$BH in THF leaves some THF occluded in the crystals which can be cleaved by Ipc$_2$BBr, causing the reagent to become impure.) To 25.96 g of Ipc$_2$BH kept at −78° C. was added ∼75 ml of CH$_2$Cl$_2$ freshly distilled over P$_2$O$_5$. To the cold suspension, Br$_2$ (6.26 g, 2.2 mL) in CH$_2$Cl$_2$ (10 mL) was added. After stirring for 15 min, the mixture was raised to 0° C. The solid Icp$_2$BH dissolves within 1 h and the color of Br$_2$ disappears. $^{11}$B NMR showed a broad singlet at δ80.00. Methanolysis gave a product which exhibited a broad singlet at δ53.00. The CH$_2$Cl$_2$ was pumped off to obtain a white solid: 31.66 g (100% yield), mp 58°-60° C., [α]$_D$−54.68 (c 2.35, CH$_2$Cl$_2$).

EXAMPLE 3

Preparation of Monoisopinocampheyldichloroborane

To monoisopinocampheylborane in ethyl ether (78 mL of 0.64 M, 50 mmol) in a 250 mL round-bottom flask was added HCl in ethyl ether (35.5 mL of 2.82 N, 100 mmol) at ice salt temperature. There was a vigorous, immediate reaction with simultaneous evolution of hydrogen. $^{11}$B NMR showed a peak at δ19.00 ppm, presumably due to an ether complex, IpcBcl$_2$.OEt$_2$. (Methanolysis shifts the peak to δ32.00, presumably due to the formation of the boronic ester IpcB(OMe)$_2$.) The ether was pumped off at aspirator vacuum and the residue distilled at 52°-55°/0.1 mm. Frothing occurs while distilling. It is advisable to use a big flask and a distillation head with a long Vigreaux column. The product is obtained as a clear liquid, the ether-free compound, IpcBcl$_2$. The yield realized was 8.9 g, 81.3%. $^{11}$B NMR neat and in CH$_2$Cl$_2$ showed a peak at δ63.00, [α]$_D$−24.00 (c 7.62, CH$_2$ Cl$_2$). Ether-free IPcBCl$_2$ is stable at room temperature for several months.

EXAMPLES 4-8

Following the method of Example 1-3, the mono- and diisopinocampheylhaloboranes set forth in Table 1 were prepared. The properties of the compounds prepared in Examples 1-3 are included.

TABLE 1

Properties of Mono- and Diisopinocampheylborohalides

| Compound | Properties |
| --- | --- |
| Ipc$_2$BF | Colorless syrup. $^{11}$B NMR δ56.00 ppm. |
| Ipc$_2$BCl | Colorless crystals. mp 54–56° C. $^{11}$B NMR δ76.0 ppm. [α]D = −67.07° (c 13.5, CH$_2$Cl$_2$). Stable in CH$_2$Cl$_2$, EE and THF. Pryophoric. Stable under nitrogen, stored at 0° C. |
| Ipc$_2$BBr | Colorless solid. mp 58–60° C. $^{11}$B NMR δ80.00 ppm. [α]D−54.68 (c 2.25, CH$_2$Cl$_2$). Cleaves ether slowly and THF rapidly (2h). Pyrophoric. Stable when stored under nitrogen at 0° C. |
| Ipc$_2$BI | White solid, extremely hydroscopic. $^{11}$B NMR δ84.0 ppm. Stable in CH$_2$Cl$_2$. Cleaves ether in 24 hours and reacts with THF instantaneously. Pyrophoric. Cannot be stored. |
| IpcBF$_2$ | Exists as IpcBF$_2$.Et$_2$O. Difficult to distill (decomp.) $^{11}$B NMR δ19.6 (IpcBF$_2$.Et$_2$O). |
| IpcBCl$_2$ | Colorless liquid. bp 52–55° 0.1 mm. $^{11}$B NMR δ63.0 ppm. [α]D −24.00°. (c 7.62, CH$_2$Cl$_2$). Pyrophoric. Fumes in air. Stable at room temperature under nitrogen. |
| IpcBBr$_2$ | Colorless liquid. bp 82–85°/ 0.7 mm. $^{11}$B NMR δ65.0 ppm. [α]D −12.41° (c 9.71, CH$_2$Cl$_2$). Pyrophoric. Fumes in air. Stable at room temperature under nitrogen. |
| IpcBI$_2$ | Could not be prepared in pure form. |

EXAMPLE 9

Reduction of 3,3-Dimethyl-2-butanone with Ipc$_2$BCl

An oven-dried 100 Ml round-bottom flask equipped wit a septum-capped sidearm, magnetic stirring bar and stopcock adaptor connected to a mercury bubbler was assembled while hot and flushed with a stream of nitrogen. Diisopinocampheylchloroborane (Ipc$_2$BCl) (8.8 g, 27.5 mmol) was transferred into the flask under a nitrogen atmosphere in a glove bag. While stirring, 3,3-dimethyl-2-butanone (3.3 mL, 25 mmol) was added via a syringe. Ipc$_2$BCl goes into solution within a few hours. The reaction mixture was quenched with methanol and followed by $^{11}$B NMR spectroscopy for the completion of the reaction. When the reaction was complete (12 days), the α-pinene formed during the reaction was removed under reduced pressure (0.1 mm Hg, 8 h). The residue was dissolved in Et$_2$O (50 mL) and diethanolamine (2.2 g) was added. The separated solid was filtered off after 2 h and washed with pentane and the combined filtrate was concentrated by distilling the volatiles. The residual liquid was distilled at 117°-119° C., giving 1.28 g (50% yield) of 3,3-dimethyl-2-butanol, [α]D+7.53° (neat) after purification by preparative gas liquid chromotagraphy on Carbowax 20 M polyethylene glycol (Union Carbide): 93% ee based on [α]$_D$8.1° (neat) for the maximum reported rotation. Gas chromatography analysis of its menthyl chloroformate derivative made from (−)- menthyl chloroformate (Aldrich Chemical Company on Supelcowax glass capillary column (15 M) showed a composition of 97.5% S+2.5% R (i.e., 95% ee).

EXAMPLE 10

Reduction of Acetophenone with Ipc$_2$BCl

Under a nitrogen atmosphere, with stirring, acetophenone (3.05 mL, 25 mmol) was added to a solution of diisopinocampheylchloroborane (9.0 g, 28 mmol) in THF (20 mL0 at −25° C. A yellow color developed immediately. The reaction was complete after 7 h at −25° C. (followed by $^{11}$B NMR after methanolysis of an aliquot). The volatiles were pumped off at aspirator pressure and the α-pinene was removed under reduced pressure (0.1 mm Hg, 8 h). The residue was dissolved in ethyl ether (100 mL0 and diethanolamine (2.2 equiv) was added. The separated solid was filtered off after 2 h and washed twice with pentane (~30 mL). The combined ether and pentane filtrates were concentrated. The residue, upon distillation (bp 118° C., 22 mm Hg) provided [S]-1-phenylethanol (2.3 g, 72% yield) [α]$^{20}$D −42.6° (neat) after purification by preparative gas liquid chromotagraphy on Carbowax 20 M; 98% ee based on −43.5° for maximum reported rotation. Gas chromotagraphy analysis of its α-methoxy-α-(trifuloromethyl)phenylacetate (made from (+)-MTPA chloride, Aldrich) on Supelcowax glass capillary column (15 m) showed a composition of 98.7% S+1.3% R (i.e., 97.4% ee), in good agreement with the optical rotation measurement.

EXAMPLE 11 yielded, on distillation, 2.12 g (70%) of the alcohol which was further purified by preparative gas chromotagraphy on Carbowax 20M. [α]$^{26}$D −42.5°; 98% ee based on [α]$_D$−43.5° for maximum reported rotation.

EXAMPLE 12

Reduction of 3-Methyl-2-butanone with IpcBCl$_2$

Under nitrogen, 3-methyl-2-butanone (2.67 mL, 25 mmol) was added with stirring to a solution of IpcBCl$_2$ (5.5 mL, 27.5 mmol) in CH$_2$Cl$_2$ 16.5 mL) at −25° C. The reaction was followed by $^{11}$B NMR after methanolysis at −25° C. and was complete in 5 h. α-Pinene was pumped off at high vacuum. Ether (50 mL) was added to the reaction flask followed by triethanolamine (12.5 mL, 3.3 eg.). The separated solid, triethanolamine borate, was filtered off, washed with pentane (2×25 mL) and the combined filtrates concentrated by distilling off the volatiles. The alcohol was collected at 110°-112° C. The yield was 1.4 g (63%); [α]$_D$+2.29°, i.e., 42.9% ee based on the maximum value reported in the literature, [α]$_D$ +5.34°. The optical purity of the alcohol was confirmed by an MTPA ester analysis on Supelcowax glass capillary column (15 M) which showed 71.55 S isomer and 28.5% R isomer, thus projecting an ee of 43% in S(+).

EXAMPLES 13-20

The chiral reduction of representative aromatic ketones with diisopinocampheylchloroborane in THF at −25° C. and the results summarized in Table 2 below. Where available, literature values for prior art reagents set out by way of comparison.

TABLE 2

Reduction of Aromatic Ketones with Ipc$_2$BCl (1), R-Alpine-Borane neat (2), R-Alpine-Borane with high pressure (3) and Binal-H (4)

| Ketone | Reactn. Time (h) | Yield % | [α]$^{20}$D,deg. | % ee Ipc$_2$BCl |
|---|---|---|---|---|
| acetophenone | 7 | 72 | −42.6 | 98$^e$,(97.4)$^f$ |
| 2'-acetonapthone | 7 | 90 | −41.1(c,6.03,EtOH) | 98$^g$ |
| 3-acetylpyridine | 15 | 65 | −43.2(c,1.86,MeOH) | 92$^i$ (92) |
| 2-acetylthiophene | 15 | 85 | −22.5(c,4.41,C$_6$H$_6$) | 91 |
| butyrophenone | 7 | 78 | −45.6(c,4.59,C$_6$H$_6$) | 100.9$^j$(98) |
| 1-indanone | 15 | 65 |  | (97) |
| isobutryophenone | 24 | 68 | −19.2 (neat) | 78$^k$ |
| pivalophenone | 12 days$^l$ | 45 | +20.5(c,1.9,C$_6$H$_6$) | 79$^{m,n}$ |

$^a$Major isomer is the S alcohol.
$^b$ From Brown et al., J. Org. Chem., 50, 1384 (1985).
$^c$From Midland et al., J. Org. Chem., 49, 1317 (1984).
$^d$From Noyori et al., J. Am. Chem. Soc., 106, 6709,6717 (1984).
$^e$Based on −43.5° (neat), MacLeod et al., J. Am. Chem. Soc., 82, 876 (1960).
$^f$Values in parenthesis are by capillary GC analyses of the (+)-α-methoxy-α-(trifluoromethyl)phenylacetates.
$^g$Based on 41.9° c 4.92, EtOH), Collier et al., J. Chem. Soc., 676 (1940).
$^h$Employs 100% excess of the reagent; reaction too slow with stoichimetric amount of the reagent, presumably due to complex formation.
$^i$Based on +46.7° for 99% ee alcohol, Uskovic et al., J. Am. Chem. Soc., 101, 6742 (1979).
$^j$Based on −45.2° C. (c, 4.81, C$_6$H$_6$).
$^k$Based on −24.6° neat, Nasipuri et al., J. Indian Chem. Soc., 44, 165 (1967).
$^l$Only 60% reaction is complete after 12 days at room temperature.
$^m$Based on 25.9° (c 2.2, C$_6$H$_6$), Vigneron et al., Tetrahedron, 32, 939 (1976).
$^n$(+) Isomer has R configuration, Clark et al., J. Org. Chem., 35, 1114 (1970).

Reduction of Acetophenone with Ipc$_2$BBr

The reduction of acetophenone with diisopinocampheylbromoborane was carried out under similar conditions as used for the reduction with the corresponding chloroborane (Example 10). Under nitrogen and stirring, acetophenone (2.91 mL, 25 mmol) was added to a solution of Ipc$_2$BBr (10.4 g, 28.6 mmol) in ethyl ether (22 mL) at −25° C. The reaction was followed by $^{11}$B NMR after methanolysis at −25° C. and was complete within 15 h. α-Pinene was removed using a high vacuum pump. Workup using diethanolamine (2.2 g)

TABLE 2

| Ketone | %ee (2)$^b$ | %ee (3)$^c$ | %ee (4)$^d$ |
|---|---|---|---|
| acetophenone | 85 | 100 | 95 |
| 2'-acetonapthone |  |  |  |
| 3-acetylpyridine | 90 | 100 |  |
| 2-acetylthiophene |  |  | 100 |
| butyrophenone |  |  |  |
| 1-indanone |  |  |  |
| isobutyrophenone |  |  | 71 |
| pivalophenone |  |  | 44 |

EXAMPLES 21-24

A comparison of the chiral induction obtained by Ipc$_2$BCl in THF at $-25°$ C. (1), and the values reported in the literature for the leading prior art reagents, Alpine-Borane at 25° C. (2) and under high pressure (3), Binal-H at $-100°$ C. (4) and NB-Enantride at $-100°$ C. (5) are set forth in Table 3.

TABLE 3

A comparison of Chiral Induction Obtained by Various Reagents in the Reduction of Representative Prochiral Ketones

| Ketone | % ee | | | | |
|---|---|---|---|---|---|
| | (1) | (2)[a] | (3)[b] | (4)[c] | (5)[d] |
| 2-butanone | 4 | 43 | (63)[e] | (24)[e] | 76 |
| 3-methyl-2-butanone | 32 | 62 | 90 | [f] | 68 |
| 3,3-dimethyl-2-butanone | 95[g] | 0.6 | | [h] | 2 |
| acetophenone | 98 | 85 | 100 | 95 | 70 |

[a]From Midland et al., J. Org. Chem., 49, 1317 (1984).
[b]From Brown et al., J. Org. Chem., 50, 1384 (1985).
[c]From Noyori, et al., J. Am. Chem. Soc., 106, 6709, 6717 (1984).
[d]From Midland et al., J. Org. Chem., 47, 2496 (1982).
[e]Value for 2-octanone.
[f]Data not available.
[g]At room temperature.
[h]Inert to the reagent.

EXAMPLES 25-31

Following the procedures described above, asymmetric reduction of representative α-tertiary alkyl ketones were carried out with Ipc$_2$BCl (neat) at 25° C. The results are summarized in Table 4 below.

TABLE 4

Asymmetric Reduction of Representative α-Tertiary Alkyl Ketones with Ipc$_2$BCl (neat) at 25° C.

| Ketone(Config.) | Reaction time | Yield % | $[\alpha]^{20}$D,deg, | % ee[a] |
|---|---|---|---|---|
| 3,3-dimethyl-2-butanone(S) | 12 d | 50 | +7.53° (neat) | 93[b](95)[c] |
| ethyl 2,2-dimethylaceto-acetate (S)[d] | 12 d | 69 | 21,3.43° (neat), 1 = 0.05 | (84)[c] |
| 2,2-dimethylcyclopentanone (S)[f] | 12 h | 71 | +24.2° (c,5.64, C$_6$H$_6$) | (98)[e] |
| 2,2-dimethylcyclohexanone (S)[f] | 12 h | 60 | | (91)[e] |
| spiro[4.4]nonan-1-one (S) | 12 h | 65 | +40.53° (c,0.6, C$_6$H$_6$) | 100[g] (95)[e] |
| methyl 1-methyl-2-oxo-cyclopentane carboxylate[h] | 5 h | | +31.2° (c,2.62, C$_6$H$_6$) | (93)[c] |
| | 60 h(−25°) | | | (96)[c] |
| 1-methyl-2-norbornanone (1S,2S) | 15 h | | | (89)[e] |

[a]Values in parentheses are by capillary GC analyses.
[b]Based on 8.1° (neat) (Newman, P., J. Am. Chem. Soc., 80, 465 (1958).
[c]Analysis of the (+)-α-methoxy-α-(trifluoromethyl)phenyl acetate.
[d]Hoffman, R. W. et al., Chem. Ber., 114, 2786 (1981).
[e]Analysis of the (−)-menthylchloroformate derivative.
[f]Based on analogy with the reduction of spiro[4.4]nonan-1-one by Ipc$_2$BCl.
[g]Based on +39.8° (c 1.5, C$_6$H$_6$). (Nakazaki, M. et al., J. Org. Chem., 46, 1147 (1981).
[h]Since the tertiary center was optically active, one-half equivalent of the reagent was used to reduce the more reactive isomer.
[i]Absolute configuration not yet assigned.
[j]Reaction carried out in THF, 1 M.

EXAMPLES 32-40

The chiral induction obtained by Ipc$_2$BCl was compared with the reported values for prior art reagents in the reduction of 3,3-Diemthyl-2-butanone. The results are summarized in Table 5.

TABLE 5

A Comparison of Chiral Induction Obtained By Various Reagents in the Reduction of 3,3-Dimethyl-2-butanone

| Reagent | Reaction Condition | %ee |
|---|---|---|
| Ipc$_2$BCl | neat, rt,12 d | 95 |
| Alpine-Borane | neat, rt, 40 d | 0.6[a] |
| Alpine-Borane | neat, 6 kbar, 9 d | inert[b] |
| Binal-H | THF, −100° C. | inert[c] |
| NB-Enantride | −100° C., THF/Et$_2$O/Pentane | 2[d] |
| amino alcohol borane[f] | THF, 0° C. | 96 |
| amino alcohol borane[f] | THF −78° C. | 86 |

[a]Noyori, R. et al., J. Am. Chem. Soc., 106, 6709, 6717 (1984).
[b]Brown, H.C., et al., J. Org. Chem., 50, 1384 (1985).
[c]Chandrasekharan, J., et al., J. Org. Chem., 50, 5446 (1985).
[d]Midland, M. M. et al., J. Org. Chem., 47, 2495 (1982).
[f]Amino alcohol prepared by treating the ester of isoleucine with excess phenyl magnesium bromide. Amino alcohol:borane ration was 1:2. Itsuno, S., et al., S. J. Chem. Soc. Perkin Trans. I., 2039 (1985).

As can be seen from the above data, the preferred haloborane of the present invention has definite advantages as a chiral reducing agent for aromatic ketones. As can be seen from Table 5, it is more efficient than Noyori's Binal-H and Alpine-Borane (without high pressure) and is close to Apline-Borane with high pressure. Further, it employs a far more available chiral auxilliary than Noyori's reagent, permitting large-scale reactions. In addition, the reduction rates are rapidly convenient.

The compounds of the present invention are also superior to most of the prior art agents for the reduction of prochiral α-tertiary ketones. Only Itsuno's isoleucine derived borane reagent may be comparable, however, the generality of that reagent for such reductions has yet to be demonstrated.

The abundant availability of both forms of α-pinene, the simple preparative procedure for the haloborane reagents of this invention, coupled with the simple operating conditions (room temperature, neat) and the easy workup provides numerous advantages over the prior art.

The invention claimed is:

1. A process for reducing a prochiral ketone to produce an optically active alcohol of high optical purity comprising reacting a prochiral ketone with a reducing agent selected from the group consisting of a mono- or diisopinocampheylhaloborane represented by the formulae: wherein Ipc is isopinocampheyl, B is boron and X is halo for from 7 hours to 24 days at a temperature of from −25° C. to ambient temperature at ambient pressure until the reaction is complete, and thereafter separating said optically active alcohol from the reaction mixture.

2. The process of claim 1 wherein the reducing agent is diisopinocampheylchloroborane.

3. The process of claim 1 wherein the reducing agent is diisopinocampheylbromoborane.

4. The process of claim 1 wherein the reducing agent is diisopinocampheyliodoborane.

5. The process of claim 1 wherein the reducing agent is diisopinocampheylfluoroborane.

6. The process of claim 1 wherein the reducing agent is monoisopinocampheyldichloroborane.

7. The process of claim 1 wherein the reducing agent is monoisopinocampheyldibromoborane.

8. The process of claim 1 wherein the reducing agent is monoisopinocampheyldiiodoborane.

9. The process of claim 1 wherein the reducing agent is monoisopinocampheyldifluoroborane.

* * * * *